United States Patent [19]

Thykeson

[11] 4,061,897
[45] Dec. 6, 1977

[54] HEATING PAD

[76] Inventor: Audrae Thykeson, 8340 SW. 65 Ave., Miami, Fla. 33143

[21] Appl. No.: 651,713

[22] Filed: Jan. 23, 1976

[51] Int. Cl.² .............................................. H05B 1/00
[52] U.S. Cl. .................................. 219/211; 128/379; 219/527; 219/529
[58] Field of Search ....................... 219/211, 527–529; 128/379, 399, 402; 126/204

[56] References Cited

U.S. PATENT DOCUMENTS

| 2,579,383 | 12/1951 | Goudsmit | 219/527 X |
| 3,748,436 | 7/1973 | Cossaboom | 219/527 X |
| 3,822,705 | 7/1974 | Pilotte | 128/379 |
| 3,839,621 | 10/1974 | Hariu | 219/527 X |
| 3,895,638 | 7/1975 | Ito | 128/379 |

FOREIGN PATENT DOCUMENTS 191,084   9/1956   Austria ................................ 128/379

Primary Examiner—C. L. Albritton

[57] ABSTRACT

A heating pad which includes adjustable belt means to securely hold the pad in engagement with the back area of a person from the lower spine up to and including the shoulders and back of the neck areas, or which may be adjustably held in engagement with the front area of a person from the lower abdomen up to and including the chest and shoulder areas.

7 Claims, 4 Drawing Figures

HEATING PAD

BACKGROUND OF THE PRESENT INVENTION

Heating pads, currently in use, are generally comprised of a thermostatically controlled heating element, disposed between two generally rectangular sheets of a suitable fabric material. Electric leads from the heating element are adapted to be plugged into any convenient electric receptacle providing 110V of electricity. A temperature control means is provided in the leads to enable the user of the heating pad to adjust it from an off position to low and high heat positions with one or more intermediate heat positions.

Heating pads of the above described nature must be constantly repositioned when in use to maintain same on the desired area of the upper portions of the body. For example, painful neck, shoulder and other areas of the body are often heat treated at home, such treatments are generally accomplished in seated or prone positions. Under the best of circumstances, when the user is awake, the heating pad constantly slips from the painful area. When the user falls asleep, the heating pad will generally become completely disengaged from the user's body.

The heating pad of the present invention, when held in a front or a back position on the upper body portion of a user by a suitable adjustable belt means, will remain in position for any desired period of time, whether the user is awake or asleep.

Therefore, one of the principal objects of the present invention is to provide a heating pad, including adjustable securing means, which may be engaged against the upper back portion of a user's body to apply heat thereto from the lower spine area up to and including the shoulder and back of the neck areas, or to the upper front body portion to apply a heat treatment to the areas extending from the lower abdomen up to and including the chest and shoulders.

A further object of this invention is to provide a heating pad wherein the adjustable securing means includes an adjustable transverse belt means connecting between the opposed side edges of the heating pad and an adjustable vertical belt means connecting between respective shoulder extension of the heating pad and the transverse belt means.

Yet another object of the instant invention is to provide an electric connection means from the electric heating element in the heating pad for plug-in engagement in a conventional 110V electric receptacle.

A further object of this invention is to provide a combination on-off and heat control means in said electric connection means.

DETAILED DESCRIPTION OF THE DRAWINGS

Figure 1:
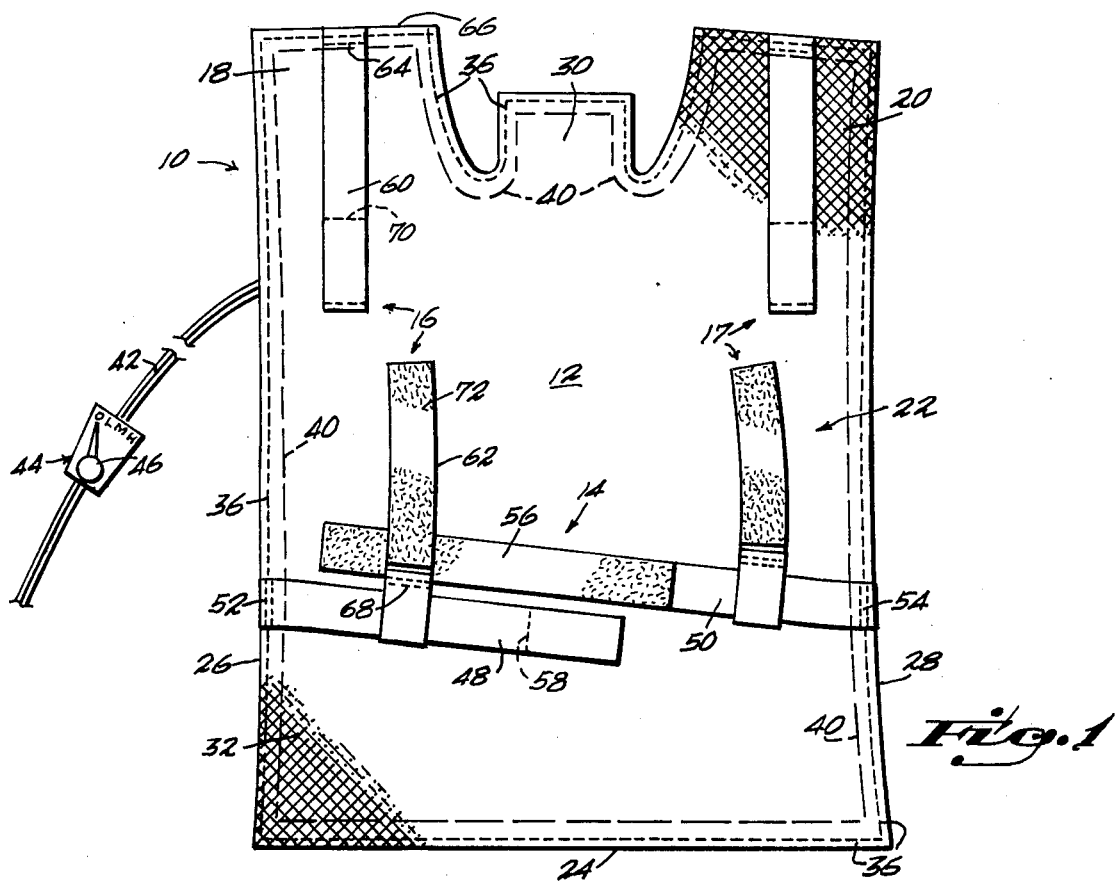
FIG. 1 is a plan view of a first side of the heating pad of the present invention.
Figure 2:
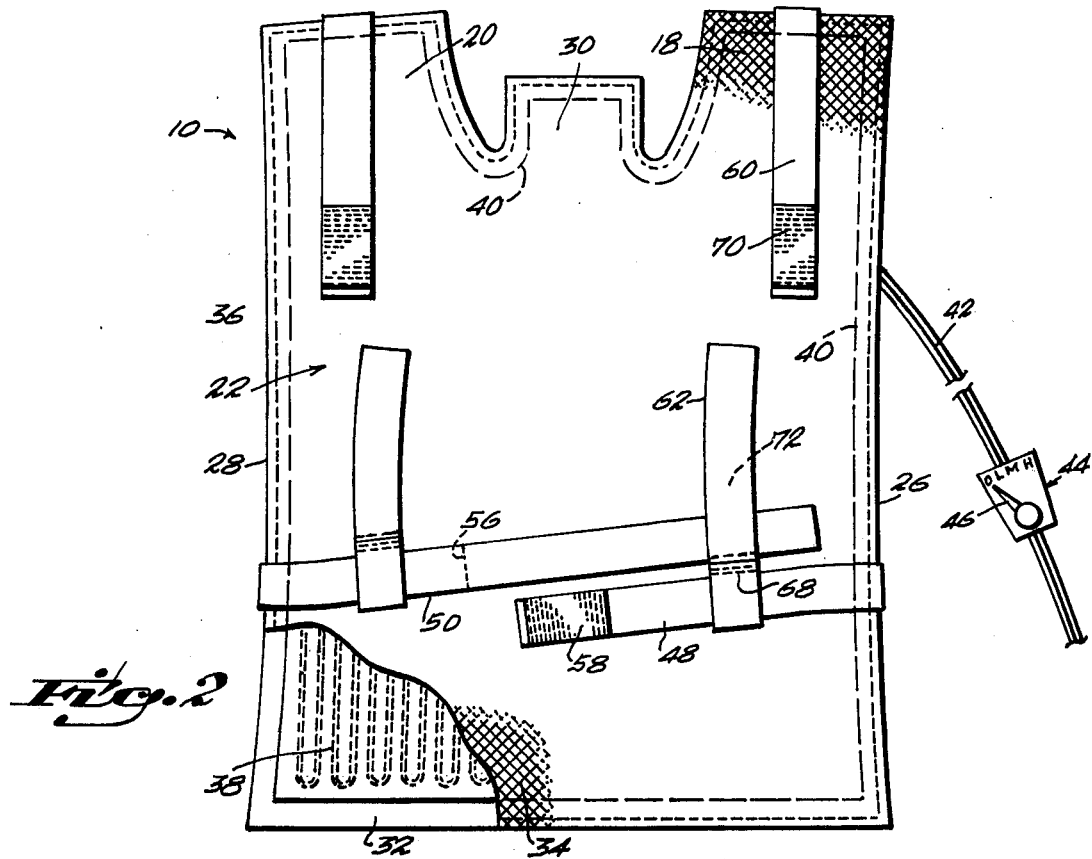
FIG. 2 is a plan view of a second side of the heating pad.

With reference to the drawings in which like reference characters designate like or corresponding parts throughout the various views and with particular reference to FIGS. 1 and 2, the heating pad of the present invention is indicated generally at 10 and includes a main body portion 12, a generally transverse belt means 14 and generally vertical belt means 16 and 17 connecting between respective shoulder covering portions 18 and 20 of the main body portion 12 and the transverse belt means 14.

The main body portion 12 is comprised of an enlarged portion 22 terminating in a bottom edge 24, opposed side edges 26 and 28, the upwardly extending opposed shoulder portions 18 and 20 and a neck portion 30 intermediate thereof. With further reference to FIGS. 1 and 2, the main body portion 12 is formed of like front and back sheets 32 and 34 of a suitable fabric material which are peripherally secured as by the stitching 36. An electric heating element 38 is sandwiched between sheets 32 and 34, generally following, in close proximity to stitching 36, the contour of the enlarged portion 22, shoulder portions 18 and 20 and neck portion 30 as indicated by broken lines 40.

The heating element is conventional in construction with the exception of its peripheral configuration as above described and needs no further description. Electric leads 42 connect between the heating element 38 and a male plug (not illustrated) for reception in a conventional receptacle. A manually operated on-off control and heat adjustment means 44 is conventionally connected in leads 42, the on-off and heat adjustment means comprises a knob and pointer 46 adjustable relative to appropriate indicia. In practice, such controls provide for adjustment between low and high heat with one or more intermediate heat positions.

Figure 3:
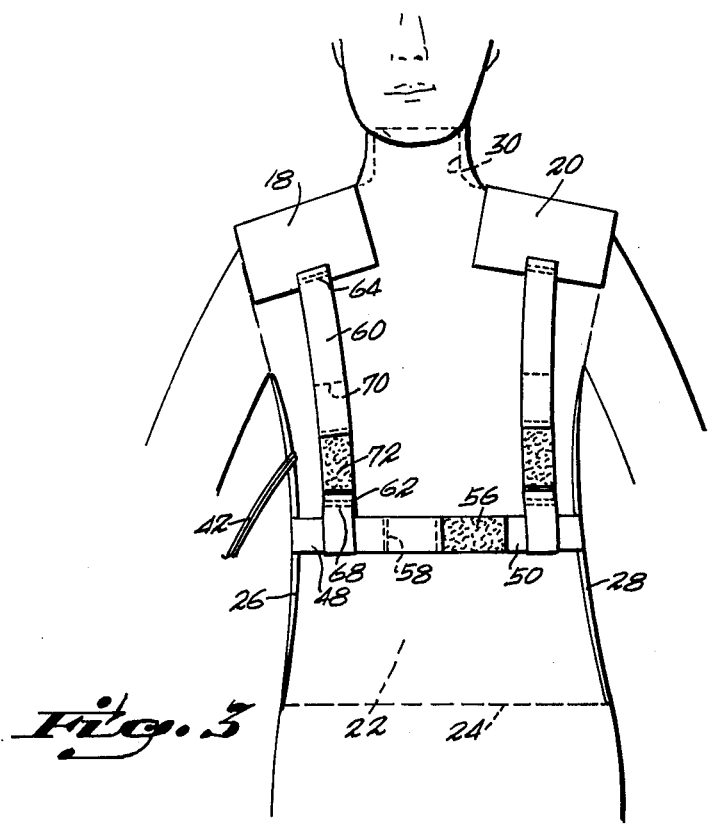
FIG. 3 is a view of the heating pad secured relative to the upper portion of a person's body in a covering relation to the back portion thereof.

With reference to the transverse belt means 14, it comprises two belt portions 48 and 50, fixed at their proximal ends as by stitching 52 and 54 to the respective side edges 26 and 28. The distal end portions, as illustrated, are preferably, adjustably connectable by means, commercially available under the trade name "Velcro," an elongated loop portion 56 and a hook portion 58 of which are fixed as by stitching to confronting faces of the respective belt portions 48 and 50. As seen in FIG. 3, the hook portion 58 may be adjustably engaged along the length of elongated loop portion 56.

Both of the vertical belt means 16 and 17 are identical in construction and will be described relative to belt means 16 which is comprised of upper and lower belt portions 60 and 62. Upper belt portion 60 is sewed at its proximal end 64 to the upper peripheral edge 66 of shoulder portion 18 and the proximal end portion of lower belt portion 62 is stitched at 68 in a loop about transverse belt portion 48 for sliding engagement therealong. "Velcro" hook and loop portions 70 and 72 are fixed to the respective upper and lower belt portions 60 and 62 for adjustable engagement therebetween in the manner described relative to transverse belt means 14.

With reference to FIG. 3, the enlarged heating pad portion 22 is disposed relative to the upper back portion of a person. The bottom edge 24 terminates in the lower spine area, the opposed side edges 26 and 28 are disposed partially around the respective sides of the person, the shoulder covering portions 18 and 20 are wrapped forwardly and downwardly around the shoulders and the neck portion 30 extends upwardly along the back of the neck.

Figure 4:
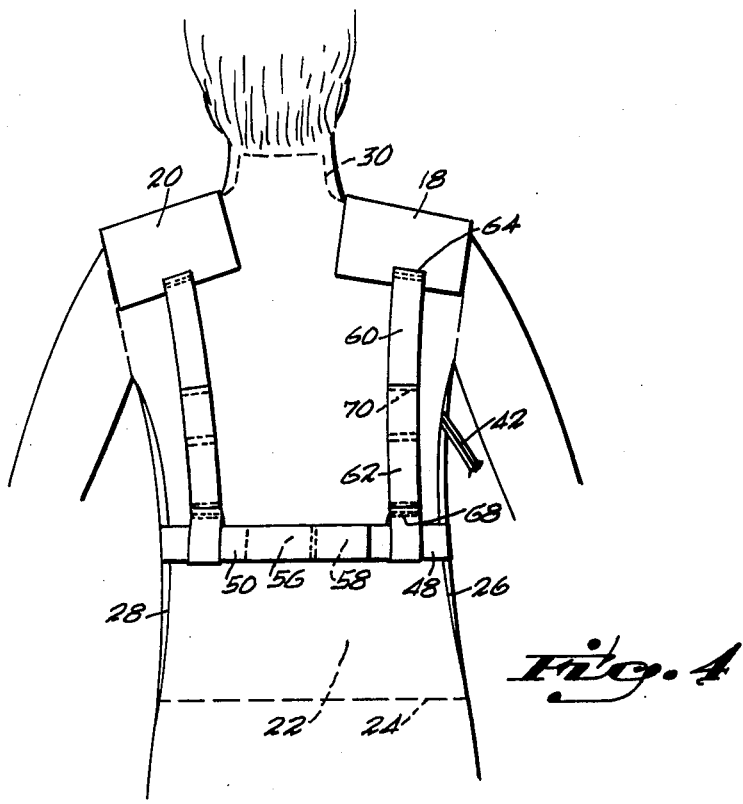
FIG. 4 is a view of the heating pad secured relative to the upper portion of a person's body in a covering relation to the front portion thereof.

FIG. 4 illustrates the enlarged heating pad portion 22 in a covering relation along the upper front portion of a person from the bottom edge 24 to the shoulder covering portions 18 and 20 which extend rearwardly and downwardly over the shoulders. Neck portion 30 extends upwardly along the front of the neck. When the heating pad 10 is switched from the back to the front of a person as illustrated, the transverse and vertical belt portions 48, 50 and 60 are pivoted about their proximal end connections and are interengaged as illustrated in FIG. 4.

It should be understood that means other than the "Velcro" attachment means may be utilized for the adjustable belt connections. For example, various types of adjustable buckle and hook means are commercially available. The sizes of the various portions of the heating pad of the present invention may be varied to cover greater or lesser body areas than those illustrated and above described.

What is claimed is:

1. A heating pad comprising:
   a main body portion formed of like front and back panels of a suitable fabric material, with a heating element sandwiched therebetween, said main body portion including an enlarged portion sized to selectively cover a predetermined portion of the back or front areas of the upper portion of a person's body, a pair of shoulder portions extending upwardly from said enlarged portion to engage over the respective shoulder areas of a person's body, and a neck portion, extending upwardly from said enlarged portion, to engage with back or front areas of a person's neck;
   a generally transverse, adjustable belt means to maintain said enlarged portion in said selected position; and
   a generally vertical, adjustable belt means, to maintain said shoulder portions in engagement over the shoulder areas.

2. The heating pad as defined in claim 1 wherein said enlarged portion is sized to generally extend upwardly from the lower spine area of a person to said shoulder and neck portions when used in said back covering position, and from the lower abdomen area of a person to said shoulder and neck portions when used in said front covering position.

3. The heating pad as defined in claim 1 wherein said front and back fabric panels are peripherally stitched together and said heating element, sandwiched therebetween, is configured to conform generally with said enlarged, shoulder and neck portions as defined by said fabric panels.

4. The heating pad as defined in claim 1 including electrical connection means from said heating element to a power source, and manual control means in said electrical connection means including on-off positions and a plurality of variable heat settings.

5. The heating pad as defined in claim 1 wherein said transverse, adjustable belt means comprises two side belt portions fixed as by stitching at their respective proximal ends to opposed side edges of said enlarged portion, and adjustable, interengaging connection means, fixed relative to the respective extended portions of said two side belt portions.

6. The heating pad as defined in claim 5 wherein said vertical, adjustable belt means comprises two pairs of upper and lower belt portions, each pair being comprised of an upper belt portion, fixed by stitching at its proximal end to a top edge of one of said shoulder portions, and a lower belt portion having a looped proximal end portion slidably engaged around one of said side belt portions; adjustable, interengaging connection means being fixed relative to respective extended portions of said upper and lower belt portions.

7. The heating pad as defined in claim 6 wherein each of said adjustable, interengaging connection means comprises a product, commercially available under the trade name "Velcro," the loop and hook positions of which are fixed as by stitching to respective confronting faces of each of said pairs of belt portions.

* * * * *